(12) United States Patent
Schwartz

(10) Patent No.: US 8,988,483 B2
(45) Date of Patent: Mar. 24, 2015

(54) MOBILE CONFERENCING SYSTEM

(76) Inventor: Ted Schwartz, San Clemente, CA (US)

( * ) Notice: Subject to any disclaimer, the term of this patent is extended or adjusted under 35 U.S.C. 154(b) by 249 days.

(21) Appl. No.: 13/489,327

(22) Filed: Jun. 5, 2012

(65) Prior Publication Data
US 2012/0306994 A1    Dec. 6, 2012

Related U.S. Application Data

(60) Provisional application No. 61/493,838, filed on Jun. 6, 2011.

(51) Int. Cl.
*H04N 7/14* (2006.01)
*G06F 19/00* (2011.01)

(52) U.S. Cl.
CPC ............ *G06F 19/3418* (2013.01); *H04N 7/142* (2013.01)
USPC .................. 348/14.05; 348/14.04; 348/14.08; 370/259; 709/203; 709/204; 715/716

(58) Field of Classification Search
CPC ........ H04N 7/14–7/148; G06F 19/34–19/3425
See application file for complete search history.

(56) References Cited

U.S. PATENT DOCUMENTS

| | | | |
|---|---|---|---|
| 6,928,490 B1 * | 8/2005 | Bucholz et al. ................ 709/249 |
| 8,172,242 B1 * | 5/2012 | Crandall ..................... 280/47.35 |
| 8,286,977 B2 * | 10/2012 | Butler et al. ................ 280/47.35 |
| 8,306,664 B1 * | 11/2012 | Wiley et al. .................... 700/259 |
| 2001/0017656 A1 * | 8/2001 | Araki et al. .................... 348/211 |
| 2003/0149342 A1 * | 8/2003 | Hanover ........................ 600/300 |
| 2004/0046487 A1 * | 3/2004 | Olivera et al. ................ 312/209 |
| 2004/0143421 A1 * | 7/2004 | Wang et al. .................... 702/188 |
| 2005/0267826 A1 * | 12/2005 | Levy et al. ....................... 705/34 |
| 2006/0051084 A1 * | 3/2006 | Sandhu ........................ 396/428 |
| 2006/0163829 A1 * | 7/2006 | Livengood et al. ...... 280/87.021 |
| 2007/0078566 A1 * | 4/2007 | Wang et al. .................... 700/259 |
| 2008/0029536 A1 * | 2/2008 | Wang et al. .................... 221/210 |
| 2008/0234666 A1 * | 9/2008 | Yadlowsky et al. ............... 606/4 |
| 2009/0055023 A1 * | 2/2009 | Walters et al. ................ 700/259 |
| 2010/0100240 A1 * | 4/2010 | Wang et al. .................... 700/259 |
| 2010/0318380 A1 * | 12/2010 | Feess et al. ....................... 705/3 |
| 2011/0288682 A1 * | 11/2011 | Pinter et al. ................... 700/259 |

* cited by examiner

*Primary Examiner* — Hemant Patel
(74) *Attorney, Agent, or Firm* — Stetina Brunda Garred & Brucker

(57) ABSTRACT

In accordance with the present invention, there is provided a remote video conferencing system which is specifically suited for use in a medical environment. The video conferencing system comprises an elongate, primary support structure such as a pole which is outfitted with castors or similar structures to allow for the selective positioning thereof in any prescribed location within an operating room. Attached to an upper region of the pole is at least one remote controlled video camera which preferably includes a laser pointer operatively coupled thereto. During a surgical procedure, the remotely located manufacturer's representative or other medical professional is able to use the internet to remotely control the video camera, and hence the laser pointer coupled thereto.

18 Claims, 3 Drawing Sheets

MOBILE CONFERENCING SYSTEM

CROSS-REFERENCE TO RELATED APPLICATIONS

This application claims the benefit of U.S. Provisional Application No. 61/493,838 entitled Mobile Video Conferencing System, filed Jun. 6, 2011.

STATEMENT RE: FEDERALLY SPONSORED RESEARCH/DEVELOPMENT

Not Applicable

BACKGROUND OF THE INVENTION

1. Field of the Invention

The present invention relates generally to video conferencing technology and, more particularly, to a mobile video conferencing system used in operating rooms to allow medical device companies to provide product support during an operation, medical procedure, or training.

2. Description of the Related Art

As is known in the medical field, typically, when a physician uses a medical device in the operating room (i.e., a knee implant, cardiac pacemaker, etc.), a representative from the medical device company which provides such device is present in the operating room as well. In most instances, the manufacturer's representative observes the procedure, and is available to provide technical input to the physician and staff on an as needed basis. However, as will be recognized, though the presence of the manufacture's representative in the operating room provides numerous potential benefits, it also carriers a fairly substantial cost.

The present invention addresses this particular issue by providing a remote videoconferencing system whereby a medical device company representative or other medical professional at any remote location outside of the operating room can have a "telepresence" inside the operating room. Advantageously, the ability for the physician to receive substantive input or feedback from a medical device manufacturer's representative without requiring that such representative be physically present in the operating room provides substantial cost savings. These, as well as other features and advantages of the present invention, will be discussed in more detail below.

BRIEF SUMMARY OF THE INVENTION

In accordance with the present invention, there is provided a remote video conferencing system which is specifically suited for use in a medical environment, wherein an individual such as a medical device company representative outside of an operating room can establish a "telepresence" inside the operating room. The video conferencing system of the present invention comprises an elongate, primary support structure such as a pole which is outfitted with castors or similar structures to allow for the selective positioning thereof in any prescribed location within an operating room. Attached to an upper region of the pole is at least one remote controlled video camera which preferably includes a laser pointer operatively coupled thereto.

During a surgical procedure, the remotely located manufacturer's representative or other medical professional is able to use the internet to remotely control the video camera, and hence the laser pointer coupled thereto. More particularly, the pan, tilt and/or zoom of the video camera may be selectively manipulated as needed to provide a desired viewing angle, and/or to point the beam generated by the laser pointer to a prescribed location in the operating room or on the patient. The audio portion of the teleconferencing system (e.g., the communication between the medical device manufacturer's representative and the surgeon) is preferably facilitated by a suitable voice over internet protocol (VOIP), such as Skype. The hardware associated with the internet enabled control of the video camera/laser pointer and voice communication is also preferably interfaced to the primary support structure.

The present invention is best understood by reference to the following detailed description when read in conjunction with the accompanying drawings.

BRIEF DESCRIPTION OF THE DRAWINGS

These, as well as other features of the present invention, will become more apparent upon reference to the drawings wherein.

Common reference numerals are used throughout the drawings and detailed description to indicate like elements.

DETAILED DESCRIPTION OF THE INVENTION

Figure 1:
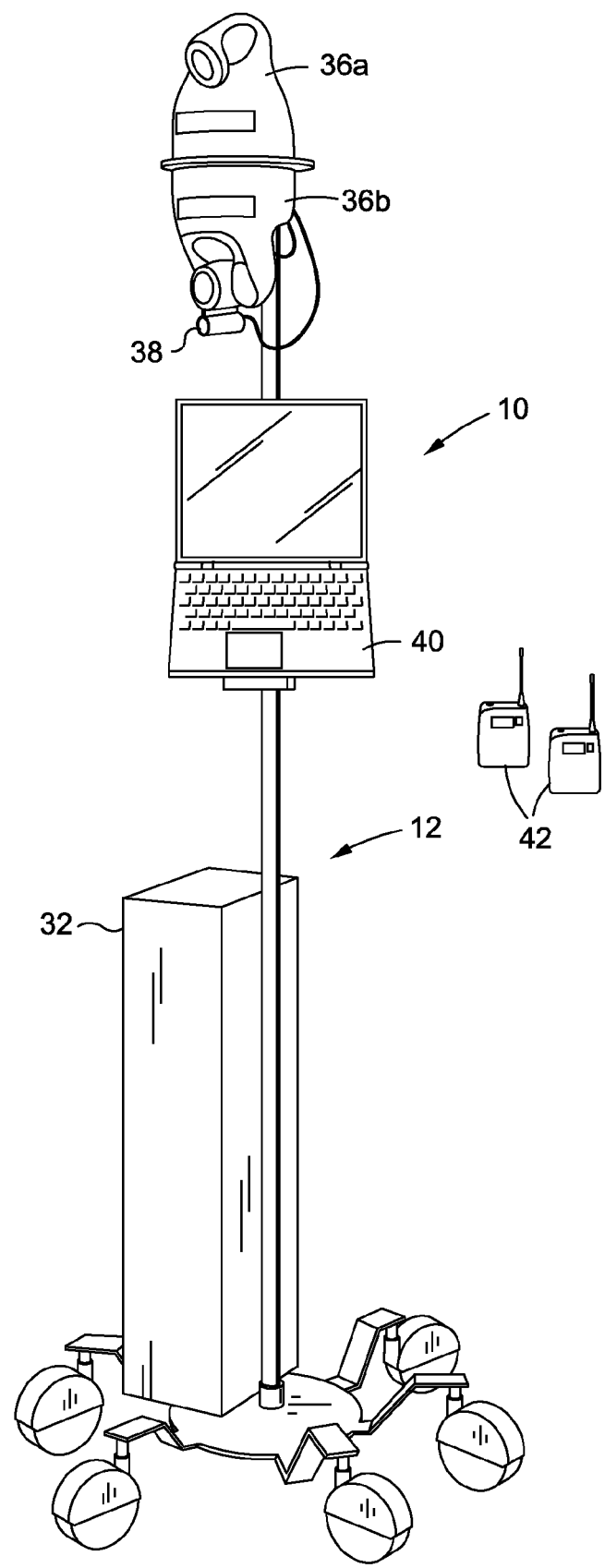
FIG. 1 is a front elevational view of the mobile video conferencing system of the present invention.
Figure 2:
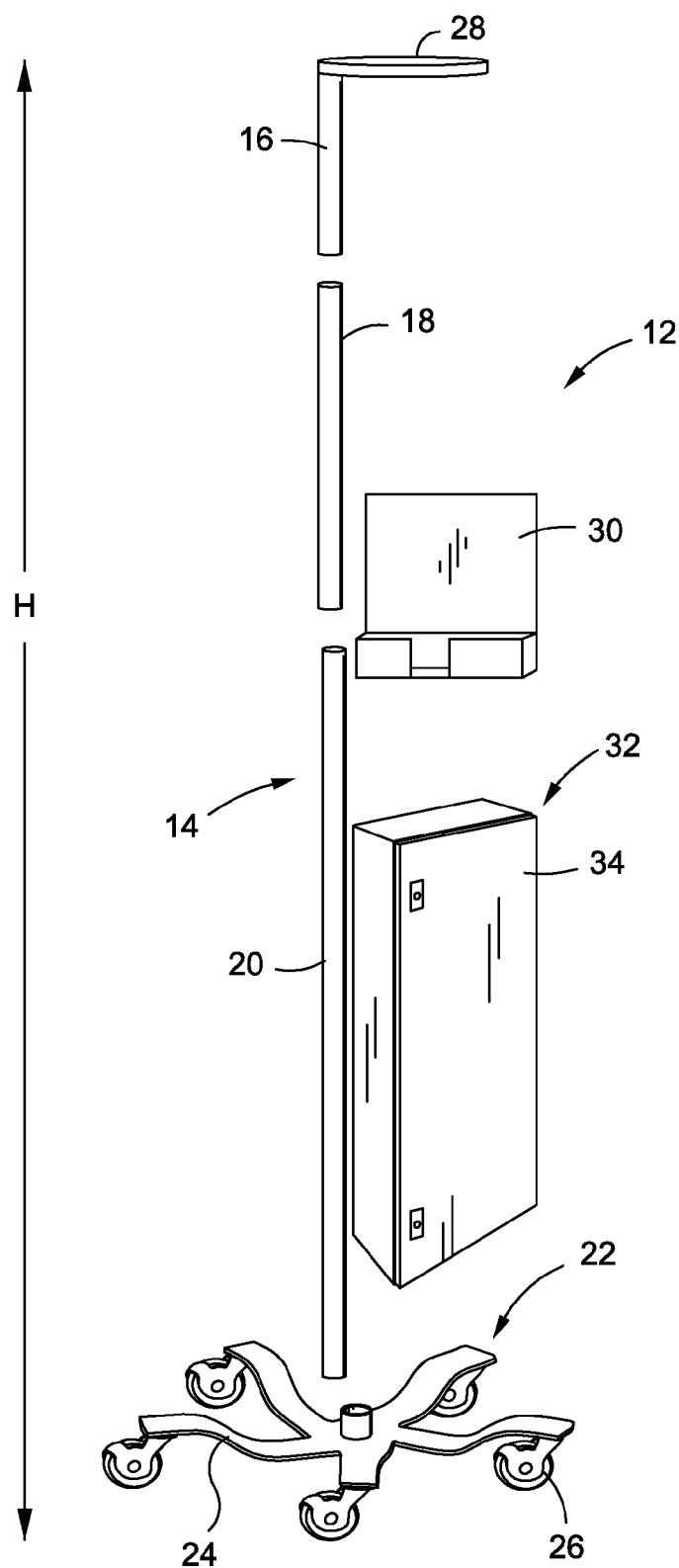
FIG. 2 is a partial exploded view of the mobile video conferencing system shown in FIG. 1.

Referring now to the drawings wherein the showings are for purposes of illustrating a preferred embodiment of the present invention only, and not for purposes of limiting the same, FIG. 1 depicts a remote video conferencing system 10 constructed in accordance with the present invention. As seen in FIGS. 1 and 2, the system 10 comprises a primary support structure 12. In an exemplary embodiment, the support structure 12 comprises an elongate pole 14. As seen in FIG. 2, the pole 14 is not a unitary structure, but rather comprises three (3) separate segments. More particularly, when viewed from the perspective shown in FIG. 2, the pole 14 comprises a top segment 16, a middle segment 18, and a bottom segment 20. The middle segment 18 preferably has a generally cylindrical, tubular configuration, and is slidably advanceable over and attachable to portions of the top and bottom segments 16, 20, each of which also has a generally cylindrical, tubular configuration. Along these lines, it is contemplated that in order to facilitate the operative interface of the middle segment 18 to each of the top and bottom segments 16, 20, the inner diameter of the tubular middle segment 18 will slightly exceed the outer diameter of each of the top and bottom segments 16, 20.

As further seen in FIG. 2, the support structure 12 further comprises a base assembly 22 which is attached to the bottom end of the pole 14, and in particular the bottom segment 20 thereof. The base assembly 22 preferably comprises a series of interconnected support struts 24, each of which has a castor 26 pivotally connected to the distal end thereof. As will be recognized, the base assembly 22 allows the primary support structure 12, and hence the entire system 10, to be easily maneuvered to any desired location upon an underlying support surface.

The support structure 12 further comprises a top shelf 28 which is attached to the top end of the pole 14, and in particular the top segment 16 thereof. The top shelf 28 is preferably attached to the top segment 16 so as to extend generally perpendicularly relative thereto, and hence the pole 14. The length of the top shelf 28 may be varied, with the particular length depicted in FIG. 2 being exemplary only.

The support structure 12 of the system 10 also includes a middle shelf 30 which is attached to the pole 14 at approximately the junction between the middle and bottom segments 18, 20 thereof. As seen in FIG. 1, within the support structure 12, the middle shelf 30 is preferably attached to the pole 14 at a location wherein a device such as a laptop or notebook computer positioned thereon is easily accessible by a standing individual of average height.

In addition to the structural features described above, the support structure 12 also includes a storage box 32 which is attached to the pole 14, and in particular the bottom segment 20 thereof. In addition to being secured to the bottom segment 20 of the pole 14, it is contemplated that the storage box 32 may also be positioned upon and secured to one or more of the support struts 24 of the base assembly 22. As shown in FIGS. 1 and 2, the storage box 32 preferably has an elongate, generally quadrangular (e.g., rectangular) configuration, with the hollow interior of the storage box 32 being accessible by an outwardly presented door 34 thereof.

In the system 10, it is contemplated that the primary support structure 12 will be constructed so as to have an overall height H (as labeled in FIG. 2) of approximately seventy-eight (78) inches. However, those of ordinary skill in the art will recognize that such height H may be increased or decreased without departing from the spirit and scope of the present invention. Additionally, it is contemplated that the pole 14, support struts 24 of the base assembly 22, top and middle shelves 28, 30 and storage box 32 will each be fabricated from a suitable metal material, though alternative non-metal materials are also contemplated to be within the spirit and scope of the present invention. Further, those of ordinary skill in the art will further recognize that the shapes of the middle shelf 30 and storage box 32 as shown in FIG. 2 are also exemplary only, and may be varied without departing from the spirit and scope of the present invention.

In addition to the primary support structure 12 described above, the system 10 of the present invention comprises two (2) remote controlled video cameras 36a, 36b which are attached to the support structure 12, and in particular to the top shelf 28 extending from the top segment 16 thereof. When viewed from the perspective shown in FIG. 1, the video camera 36a is secured to the top surface of the top shelf 28, with the video camera 36b being secured to the opposed lower surface thereof. As will be discussed in more detail below, the pan, tilt and/or zoom of each of the video cameras 36a, 36b may be remotely controlled via the internet by an operator (e.g., a medical professional) located remotely from the operating room or other location in which the system 10 is located. Exemplary video cameras 36a, 36b suitable for use in the system 10 are available from the Axis Communications Corporation as Model No. 214 PTZ.

The system 10 further comprises a laser pointer 38 which is operatively coupled to one of the video cameras 36a, 36b. As shown in FIG. 1, the laser pointer 38 is attached to the lower video camera 36b, though such laser pointer 38 may alternatively be coupled to the upper video camera 36a without departing from the spirit and scope of the present invention. Importantly, the laser pointer 38 is mounted to the video camera 36b at a location wherein it is moveable concurrently with the non-stationary portion of the video camera 36b. In addition, the positioning of the laser pointer 38 relative to the video camera 36b is such that the laser beam generated by the activation of the laser pointer 38 extends in generally parallel relation to the view axis of the circularly figured camera lens of the lower video camera 36b, as is apparent from FIG. 1.

In the system 10, both the video cameras 36a, 36b and laser pointer 38 are electrically connected to a medical grade power strip (not shown) which is preferably disposed within the interior of the storage box 32. An exemplary power strip suitable for use in the system 10 is manufactured by Tripp Lite, Inc., as Model No. PS-615-HG-OEM. Such power strip includes a power cord extending therefrom which may be interfaced to a conventional wall outlet, thus supplying power to both the video cameras 36a, 36b and laser pointer 38. In the system 10, the electrical connection between the video cameras 36a, 36b, laser pointer 38 and power strip is facilitated by a suitable modality, such as wiring, which may be advanced through the interiors of the tubular top, middle and bottom segments 16, 18, 20 of the pole 14.

In addition to the foregoing, the system 10 comprises a computer 40, such as a laptop or notebook computer, which is positioned upon and secured to the middle shelf 30. The computer 40 may be powered by an on-board battery, or alternatively may be electrically connected to the aforementioned power strip within the storage box 32 by suitable wiring which extends within the hollow interior of the pole 14. In a preferred embodiment, the computer 40 used in the system 10 will include external speakers which are also attached to the middle shelf 30.

In addition to the power strip, also mounted within the interior of the storage box 32 is a router (not shown) of the system 10. An exemplary router suitable for use in the system 10 is manufactured by Cisco Systems, Inc. as Model No. RV082. The router is itself electrically connected to the power strip which is adjacent thereto within the interior of the storage box 32, and is further operatively interfaced to the video cameras 36a, 36b and computer 40. In this regard, the cabling used to facilitate the interface of the video cameras 36a, 36b and computer 40 to the router is also preferably advanced through the interiors of the tubular top, middle and bottom segments 16, 18, 20 of the pole 14.

As further seen in FIG. 1, though they are not attached to the primary support structure 12 as are other components of the system 10, such system 10 further includes a pair of wireless lapel microphones 42 which are adapted to wirelessly communicate with the computer 40. Exemplary microphones 42 suitable for use in the system 10 are manufactured by Sennheisser, Inc. as Model No. ew112-pG3.

Figure 3:
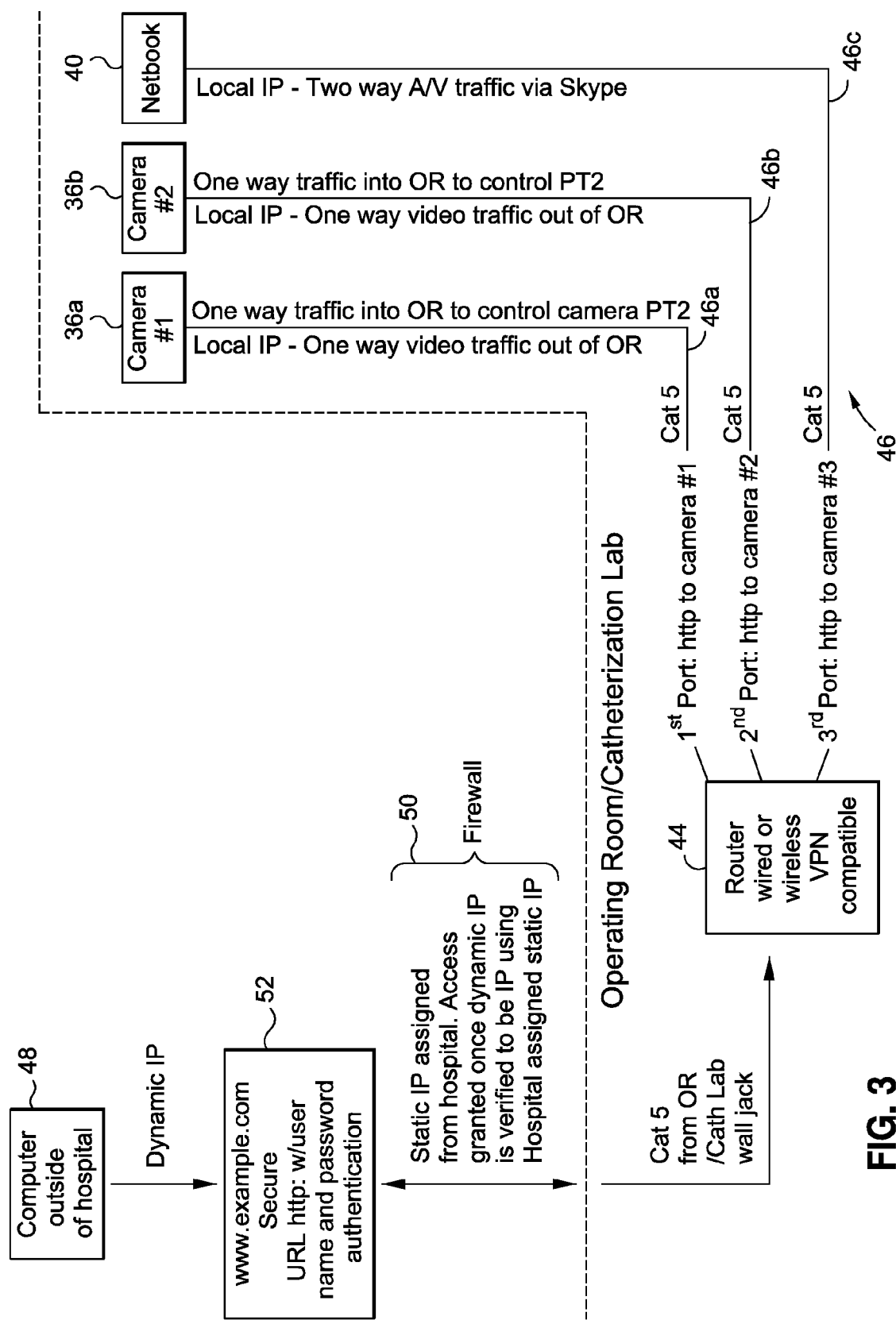
FIG. 3 is a flow chart providing an exemplary operational protocol for the mobile video conferencing system of the present invention.

Having thus described the various structural features of the system 10, the functional features of the same deployed in, for example, an operating room environment will now be described with specific reference to FIG. 3.

As indicated above, the storage box 32 includes an Internet Protocol (IP) router 44, which is preferably compatible with Virtual Private Network (VPN) protocols. The video cameras 36a, 36b and the computer 40 are independently connected to the router 44 via separate network connections 46a, 46b, and 46c, respectively, and are part of a local area network 46. Thus, each device is assigned a unique local area IP address. At the physical layer, the network connections 46a, 46b, and 46c are CAT 5 cables, though in some embodiments wires may be eliminated altogether and instead utilize Wireless LAN technologies. Those having ordinary skill in the art will recognize the attendant modifications to the client network devices and access points for such implementation.

Various embodiments of the present disclosure contemplate an end-to-end connection between a remote computer 48 located outside of the operating room, and the devices in the operating room, including video cameras 36a, 36b and the computer 40. One possible utility is in a medical device company representative or other personnel establishing a "telepresence" inside the operating room. In this regard, the video cameras 36a, 36b generate video feed data of the events transpiring in the operating room, which is transferred to the router 44 via the network connections 46a, 46b. Bi-directional video conferencing is facilitated by a suitable voice over internet protocol (VOIP) application such as Skype that is being executed on the computer 40. Video and audio data from the teleconferencing application is likewise transferred to the router 44 via the network connection 46c.

Generally, data from the devices on the local area network 46 is consolidated and directed upstream by the router 44. In this instance, upstream refers to a single network connection to the operating room. A typical hospital, or any facility for that matter, may have multiple network connections located throughout. The device connected thereto may itself be part of a wider local area network of the facility, with the upstream connection to independent networks outside of the hospital such as the Internet being regulated by a firewall 50. The firewall 50 is understood to have a static IP address assigned thereto.

Access from the remote computer 40 over the Internet to the router 44 and hence the video cameras 36a, 36b and the computer 40, is granted via a website 52. Various access control modalities, including user name and password authentication, are enforced by the website 52. Furthermore, data traffic between the computer 48 and the website 52 may be over TLS/SSL (transport layer security/secure sockets layer). Upon presenting the proper credentials, the operator of the remote computer 40 is granted access to the video stream and teleconferencing data from the router 44 via the based interface on the website 52.

It will be appreciated that the firewall 50 and the router 44 handle incoming traffic from the remote computer 48 in addition to the outgoing traffic to the remote computer 48 as discussed above. For instance, video and audio teleconferencing data generated by the remote computer 48 is transmitted to the hospital firewall 50 and redirected to the router 44 by the same. The router 44 then directs the data to the computer 40, for viewing by personnel in the operating room. Furthermore, the viewing angle of the video cameras 36a, 36b can be manipulated remotely, with such control input being provided to the website 52. The camera control data is likewise transmitted to the hospital firewall 50 and redirected to the router 44. The video cameras 36a, 36b respond to the control data by adjusting its positioning accordingly. It is expressly contemplated that the laser pointer 38 may be similarly activated and deactivated from the remote computer 48.

This disclosure provides exemplary embodiments of the present invention. The scope of the present invention is not limited by these exemplary embodiments. Numerous variations, whether explicitly provided for by the specification or implied by the specification, such as variations in structure, dimension, type of material and manufacturing process may be implemented by one of skill in the art in view of this disclosure. For example, the pole may be configured to be telescoping, thus allowing for the selective adjustment thereof to a shorter profile for greater ease of transport or storage. Along these lines, the top and middle shelves 28, 30 (and hence the components mounted thereto) may be selectively detachable from the pole 14 for transport and/or storage purposes.

What is claimed is:

1. A remote medical procedure conferencing system for linking personnel at an operating site with an internal network and a remote site external to the network, the system comprising:

a virtual private network server connected to an internal network of the operating site and accessible from the remote site;

a router connected to the virtual private network server, the router being part of the internal network of the operating site; and first and second video capture devices and one or more video display devices installed at the operating site and communicatively linked to the router over the internal network, wherein the first and second video capture devices are mounted in vertical axis relative to each other;

wherein the virtual private network server receives video data from the first and second video capture devices, for transmission to the remote site upon being authenticated to the virtual private network server, and wherein the virtual private network server transmits video data received from the remote site for transmission to the one or more video display devices.

2. The system of claim 1, wherein a one of the video display devices is a computer system including a display screen, and one of the first and second video capture devices is a camera installed on the computer system.

3. The system of claim 2, wherein the computer system includes videoconferencing software loaded thereon operative to transmit and receive the video data to and from the remote site.

4. The system of claim 2, wherein a network connection between a one of the first and second video capture devices and the router is wired.

5. The system of claim 4, wherein the wired network connection is Category-5 cable.

6. The system of claim 1, wherein each of the first and second video capture devices and each of the one or more video display devices are assigned a unique internal Internet Protocol address.

7. The system of claim 6, wherein the virtual private network server has a static Internet Protocol address, with the unique Internet Protocol addresses of the first and second video capture devices and the one or more video display devices being abstracted from the remote site.

8. The system of claim 1, wherein a network connection between a one of the first and second video capture devices and the router is wireless.

9. The system of claim 1, wherein the first and second video capture devices are receptive to camera control commands received from the remote site to adjust viewing angles.

10. The system of claim 1, wherein a network connection between the remote site and the virtual private network server is a secure data transfer link.

11. The system of claim 1, further comprising:

a firewall associated with the operating site and connected to an upstream link of the router;

wherein the virtual private network server establishes a static data communication link to the firewall.

12. The system of claim 11, wherein the virtual private networks server is a website.

13. A support structure for use in a remote medical procedure conferencing system for linking personnel at an operating site with an internal network and a remote site external to the network, the support structure comprising:

an elongate pole having a longitudinal axis and opposed upper and lower end portions;

a base assembly attached to the lower end portion of the pole;

a shelf attached to the pole at the top portion thereof, the shelf having an upper surface and an opposed lower surface;

a storage box attached to the pole between the shelf and the base assembly;

a first video camera attached to the upper surface of the shelf, the first video camera being configured to be remotely controllable by an operator at the remote site to adjust any one of, or any combination of the pan, tilt or zoom of the video camera;

a second video camera attached to the opposed lower surface of the shelf; and a laser pointer attached to one of the first and second video cameras and concurrently movable therewith relative to the pole.

14. The support structure of claim 13 further comprising a router disposed within the storage box and operatively interfaced to each of the first and second video cameras.

15. The support structure of claim 14 further comprising a computer operatively interfaced to the router and to each of the first and second video cameras.

16. The support structure of claim 15 further in combination with a pair of wireless lapel microphones which are each adapted to wirelessly communicate with the computer.

17. The support structure of claim 13, wherein the first and second video cameras are attached to the upper and lower surfaces of the shelf in vertical axis relative to each other.

18. The support structure of claim 13, wherein the first and second video cameras are attached to the upper and lower surfaces of the shelf in vertical alignment relative to each other along an axis being offset from the longitudinal axis of the pole.

* * * * *